United States Patent [19]

Lerman

[11] 4,372,298
[45] Feb. 8, 1983

[54] KNEE BRACE

[75] Inventor: Max Lerman, Beverly Hills, Calif.

[73] Assignee: U.S. Manufacturing Co., Pasadena, Calif.

[21] Appl. No.: 285,424

[22] Filed: Jul. 20, 1981

[51] Int. Cl.³ .............................................. A61F 3/00
[52] U.S. Cl. .................................... 128/80 C; 128/88
[58] Field of Search .................... 128/80 C, 80 F, 88, 128/87 R, 165; 2/22, 24

[56] References Cited

U.S. PATENT DOCUMENTS

| | | | |
|---|---|---|---|
| 3,581,741 | 6/1971 | Rosman et al. | 128/80 C |
| 4,183,099 | 1/1980 | Lacey | 2/24 |
| 4,271,831 | 6/1981 | Deibert | 128/80 C |

Primary Examiner—John D. Yasko
Attorney, Agent, or Firm—Christie, Parker & Hale

[57] ABSTRACT

A knee brace comprises generally U-shaped upper and lower support members for fitting around the upper and lower leg above and below the knee joint; two pairs of upper and lower support arms extending downwardly and upwardly, respectively, from the upper and lower support members along opposite sides of the patient's upper leg; and polycentric hinges for pivoting the upper support arms to the lower support arms adjacent lateral and medial sides of the knee joint. Floating condyle pads are affixed to fixed inside portions of the polycentric hinges. The condyle pads are held in direct contact with the lateral and medial sides of the patient's knee joint. The condyle pads are restrained from rotational movement but are hinged so they can pivot toward or away from each other about common generally vertical axes within the space between the polycentric hinges. The condyle pads can be spring-biased inwardly by their hinges for contact with opposite sides of the knee joint during swinging movement of the upper and lower leg about a horizontal axis. Flexible and longitudinally elastic upper and lower straps are releasably secured to the upper and lower limb support members. The straps extend in opposite directions away from the sides of the upper and lower support members. This provides a de-rotation strapping system which inhibits twisting of the lower leg relative to the upper leg about a vertical axis.

16 Claims, 7 Drawing Figures

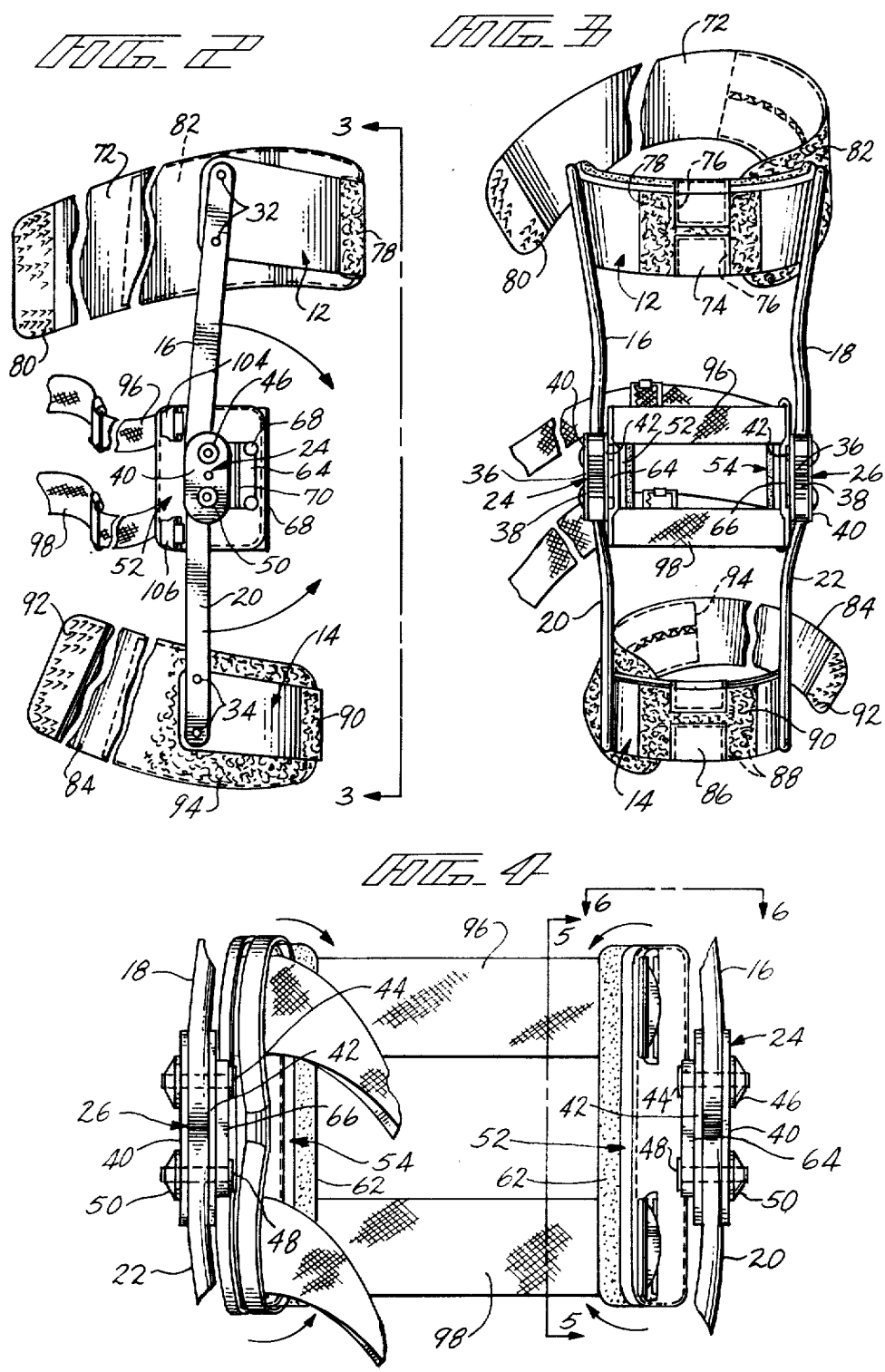

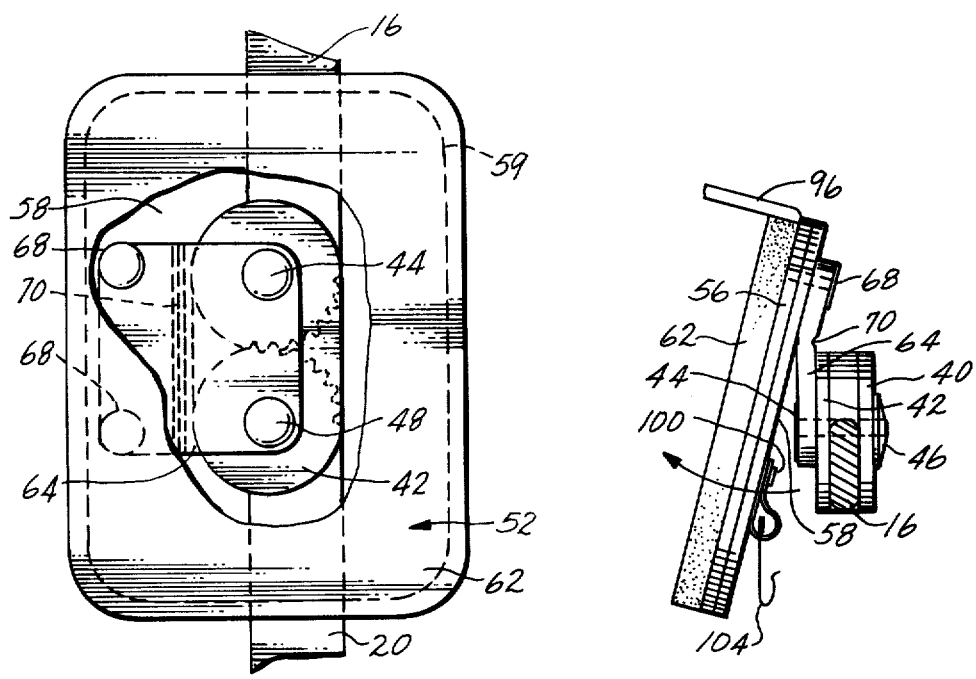

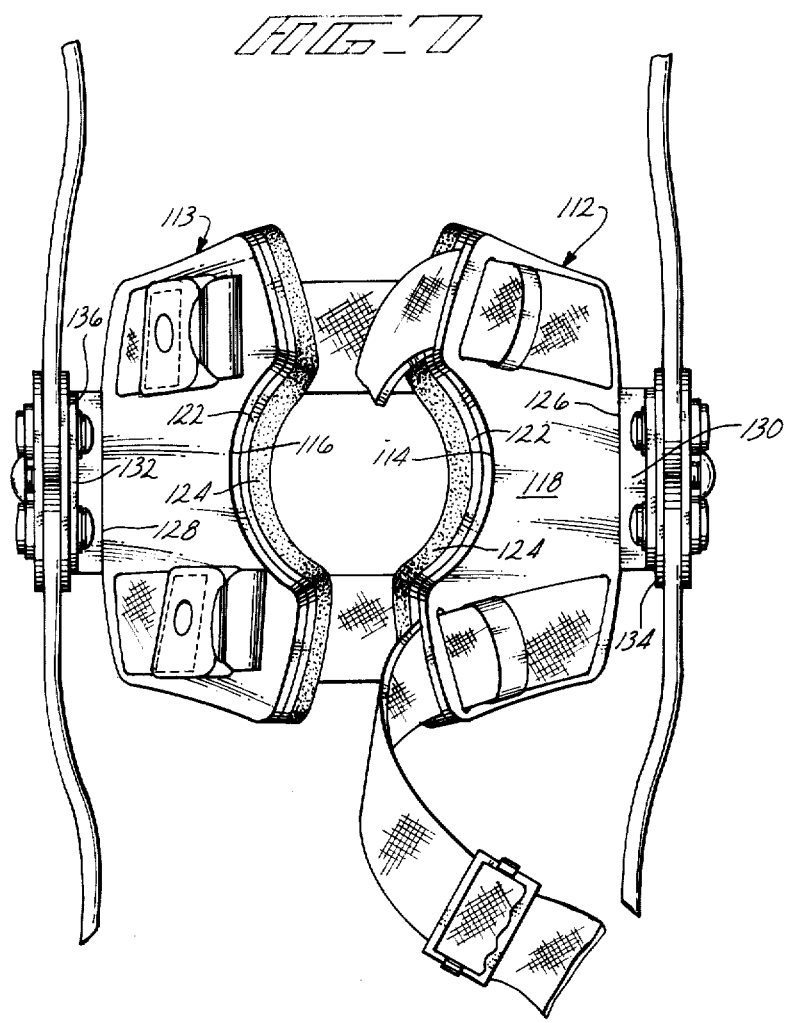

KNEE BRACE

BACKGROUND OF THE INVENTION

1. Field of the Invention

This invention relates to knee braces, and more particularly to an improved knee brace for supporting the knee to prevent certain motion of the knee joint that could injure the ligaments of the knee, while allowing the knee joint to otherwise bend safely about a horizontal axis through the knee.

2. Description of the Prior Art

A knee brace can be worn by a post-operative patient who has had knee surgery. Knee braces also are worn by persons who suffer knee instabilities and by other persons engaged in sporting activities to prevent sporting injuries to the knee. The common purpose of a knee brace is to provide exterior support for the knee to prevent any unnatural movements of the knee joint which could injure or re-injure the knee ligaments, while allowing the normal swinging movement of the knee joint about a horizontal axis through the knee (viz., forward and backward movement of the lower leg or tibia relative to the upper leg or femur, as in a normal walking motion). One type of motion to be prevented by a knee brace is a sudden movement of the upper and lower legs to one side or the other. Another type of motion to be restrained is a twisting or rotation of the lower leg relative to the upper leg about a vertical axis.

A prior art knee brace for supporting the knee in the manner described above is disclosed in U.S. Pat. No. 3,669,105 to Castiglia. The knee brace disclosed in that patent has a pair of lateral uprights extending along the outside of the leg and articulated at the outside of the knee joint by a single axis pivot pin. Upper and lower contact pads attached to the ends of the uprights contact the outside of the thigh and lower leg above and below the knee joint. Curved, rigid bars extend from the upper and lower contact pads around and in front of the upper and lower leg to the inside of the knee joint where the ends of the bars are interconnected by another single axis pivot pin. A condyle pad attached to the inside pivot pin engages the inside of the patient's knee joint. The pad rotates about the pivot pin axis independently of the upper and lower curved bars. A pair of wide elastic rubber straps attached to the upper and lower contact pads are used to encircle the leg above and below the knee joint to support the curved bars on the upper leg and lower leg. A smaller elastic strap is attached to the lower contact pad and is spiraled upwardly around the back of the knee and attaches to the upper contact pad. This strap is intended to provide a de-rotation capability preventing the lower leg from rotating or twisting relative to the upper leg about a vertical axis.

The knee brace in the Castiglia patent suffers from a number of shortcomings which are overcome by the present invention. For example, the curved bars supported on the front of the tibia and the femur can be discomforting to the patient, particularly the lower curved bar that can cause pressure over the crest of the tibia. The present invention provides a knee brace which is more comfortable, in part, because it eliminates pressure points at the front of the legs. In addition, the knee brace of this invention provides better overall contact with the sides of the knee joint, by providing a pair of floating condyle pads with a unique hinge arrangement that applies spring biased pressure that maintains total contact between the condyle pads and the knee joint through the full range of motion at the knee. Further, an improved de-rotation arrangement is provided that is less cumbersome and more effective in preventing undesired twisting of the lower leg relative to the upper leg.

SUMMARY OF THE INVENTION

Briefly, one embodiment of this invention provides a knee brace having a pair of pivotally interconnected inner support arms for extending along the inside of the upper and lower leg and pivoting adjacent the knee joint, and a pair of pivotally interconnected outer support arms for extending along the outside of the upper and lower leg and pivoting adjacent the knee joint. An upper curved support member is attached to upper ends of the inner and outer support arms for fitting around the back of the patient's upper leg above the knee joint. A lower curved support member is attached to lower ends of the inner and outer support arms for fitting around the back of the patient's lower leg below the knee joint. A pair of inner and outer floating condyle pads are mounted adjacent the pivot points of the inner and outer support arms for contacting the inner and outer sides of the knee joint. Each condyle pad is hinged to pivot through an angle about a corresponding generally vertical axis toward or away from the other condyle pad within the space between the pivot points adjacent the knee joint. Both condyle pads are hinged to apply inward tension for maintaining essentially continuous contact with the inner and outer sides of the knee joint during normal pivoting motion of the knee joint.

In one embodiment, an upper flexible strap is attached to the upper curved support member so that the upper strap can be stretched to extend around and in direct contact with the patient's upper leg above the knee joint. A lower flexible strap is attached to the lower curved support member so that the lower strap can be stretched to extend around and in direct contact with the patient's lower leg below the knee joint. The upper and lower straps provide a de-rotation strapping system in which the two straps extend in opposite directions away from the upper and lower support members for use in wrapping the straps in opposite directions around the upper and lower legs. The tightly wrapped upper and lower straps cooperate with the upper and lower support members to prevent undesired twisting or rotation of the upper and lower legs.

These and other aspects of the invention will be more fully understood by referring to the following detailed description and the accompanying drawings.

DRAWINGS

FIG. 2 is a side elevation view taken on line 2—2 of FIG. 1;

FIG. 3 is a rear elevation view taken on line 3—3 of FIG. 2;

FIG. 4 is a fragmentary front elevation view taken on line 4—4 of FIG. 1;

FIG. 5 is a fragmentary side elevation view, partly broken away, taken on line 5—5 of FIG. 4;

FIG. 6 is a top elevation view, partly in cross section, taken on line 6—6 of FIG. 4; and FIG. 7 is a fragmentary front elevation view showing an alternative knee brace according to the principles of this invention.

DETAILED DESCRIPTION

Figure 1:
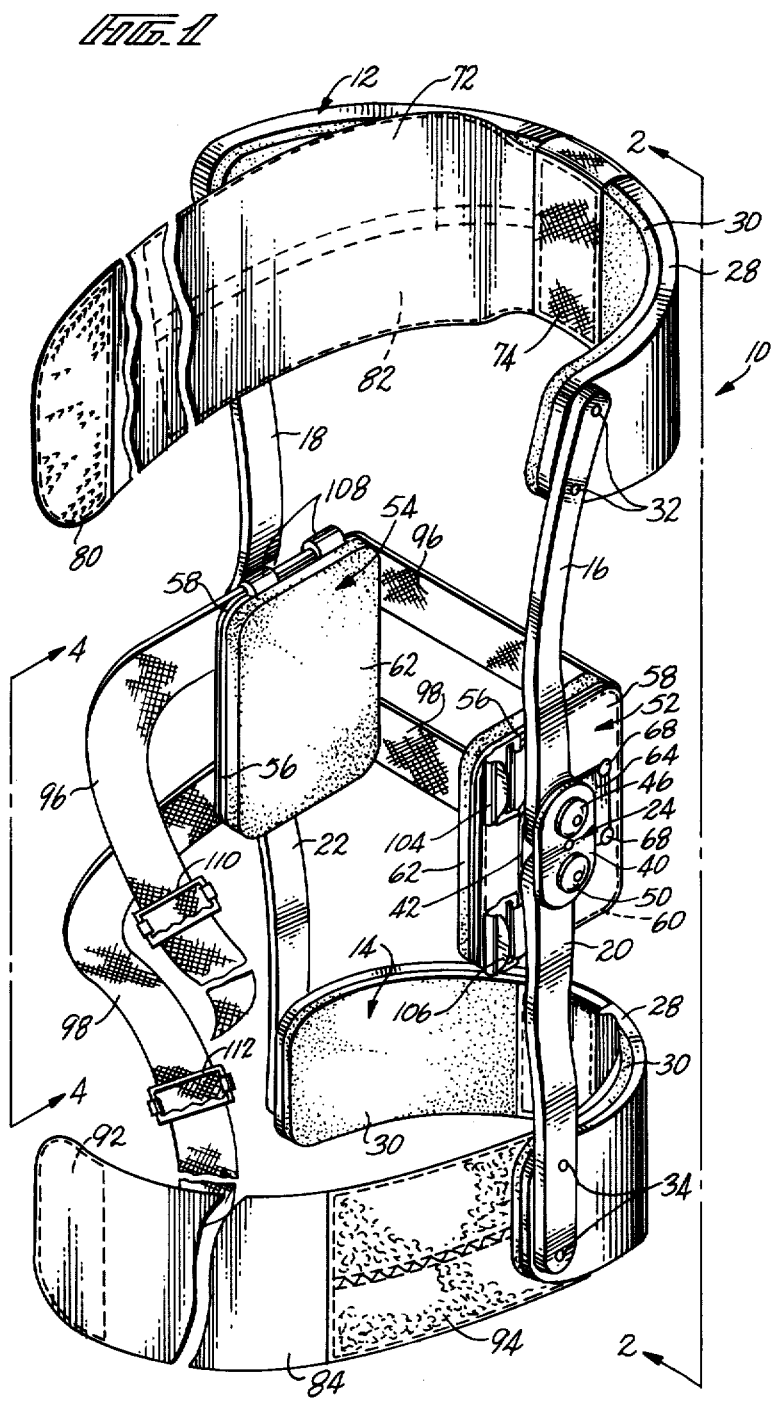
FIG. 1 is a prespective view showing a knee brace according to principles of this invention.

The drawings illustrate a knee brace 10 constructed according to principles of this invention for supporting the ligaments of the knee. As shown best in FIG. 1, the knee brace generally includes a U-shaped upper limb support member 12 and a U-shaped lower limb support member 14 spaced below the upper limb support member. A pair of horizontally spaced apart rigid, elongated lateral and medial upper support arms 16 and 18 are affixed to the opposite outer ends of the upper U-shaped support member. The upper support arms extend downwardly toward a horizontal rotational axis which extends from side to side through the knee joint. The knee joint, for simplicity, can be considered to provide rotation about a single horizontal axis; but in reality the knee joint provides rotation about a polycentric axis. A pair of horizontally spaced apart rigid elongated lateral and medial lower support arms 20 and 22 are affixed to opposite outer ends of the lower U-shaped support member. The lower support arms extend upwardly toward the horizontal rotational axis through the knee joint. The ends of the upper and lower arms on the lateral and medial sides of the knee joint are interconnected by corresponding lateral and medial polycentric hinges 24 and 26, respectively. The hinges allow the upper and lower support arms, on both sides of the brace, to swing in unison about a polycentric axis through the knee joint.

The outer face of each U-shaped support member comprises a narrow semi-rigid plastic member 28. The inner face of each U-shaped support member comprises a resilient layer 30 of padding such a foam rubber or polyurethane foam. The upper and lower U-shaped members open in the same direction and are substantially parallel to one another when the brace is in the extreme upright position shown in FIG. 1. The enclosed area within the upper U-shaped support member is larger than that of the lower support member, and the upper and lower support members are shaped to fit around the back of the patient's upper and lower leg at points spaced above and below the knee joint. Each semi-rigid U-shaped member 28 is sufficiently rigid to provide adequate support for the upper and lower leg, but each member is also sufficiently flexible to be conformed to circumferential variations in the shape of the back of patient's upper and lower leg.

The upper and lower lateral and medial support arms are narrow rigid metal bars, preferably made of stainless steel. Separate pairs of rivets 32 rigidly secure the upper lateral and medial support arms 16 and 18 to the outer face of the upper semi-rigid support member 28. Similarly, separate pairs of rivets 34 rigidly secure the lower lateral and medial support arms 20 and 22 to the outer face of the U-shaped lower support member. The upper and lower support arms extend toward one another (along the lateral and medial sides of the patient's leg during use). More specifically, the upper and lower lateral support arms are aligned generally in a common vertical plane on the outer side of the patient's leg, and the upper and lower medial support arms are aligned generally in another common vertical plane along the inner side of the patient's leg.

The ends of the upper and lower support arms terminate adjacent one another at the lateral and medial polycentric hinges. Polycentric hinges are known in the art. In each polycentric hinge, the lower end of each upper arm has gear teeth 36 (see FIG. 3) that mesh with cooperating gear teeth 38 on the upper end of the adjacent lower support arm. A metal outer hinge plate 40 and a cooperating metal inner hinge plate 42 are aligned along the inner and outer faces of the upper and lower support arms so as to overlap the gear teeth interconnecting the ends of the support arms. At each polycentric hinge, an upper pivot pin 44 extends through the inner plate, the lower end of the upper arm, the outer plate, and an internally threaded nut 46. The upper pivot pins on opposite sides of the brace are aligned on a common horizontal axis extending through the lower end portions of the lateral and medial upper arms 16, 18. A lower pivot pin 48 extends through the inner plate, the upper end of the lower arm, the outer plate, and an internally threaded nut 50. The lower pivot pins on opposite sides of the brace extend through lower portions of the upper arms along a common horizontal axis spaced below the axis on which the upper pivot pins 44 are aligned.

The polycentric hinges allow the upper support arms to pivot in unison through an angle relative to the lower support arms about a horizontal polycentric axis through the knee joint. The cooperating gears of the polycentric hinges make it possible for the lower support arms to pivot automatically when the upper support arms pivot, and vice versa. The precise location of the polycentric pivot axis in effect varies as the angle between the upper and lower support arms varies. The upper and lower support arms are only able to pivot in a backward direction (toward each other in the direction of the arrows in FIG. 2) from the substantially vertical orientation shown in FIG. 2, or in a forward direction toward the substantially vertical orientation shown in FIG. 1 and in FIG. 2. At each polycentric hinge, the interconnected end portions of the upper and lower support arms provide stops for limiting relative angular movement of the upper arms and the lower arms at both ends of travel. Enlarged portions of the upper and lower arms adjacent opposite ends of the gear teeth rotate into engagement with each other and bind to limit further angular travel for providing the stops at both ends of travel. One set of stops limits forward rotation of the upper and lower support arms (in the direction opposite to the arrows in FIG. 2) to the substantially vertical orientation shown in FIG. 2. The other pair of stops limits backward rotation of the upper and lower support arms (in the direction of the arrows in FIG. 2) to angles of about plus and minus 30 degrees relative to horizontal.

The anatomical knee joint is not a single-axis joint, and the polycentric hinges provide a better way of simulating the swinging movement of the anatomical knee joint than single-axis hinges at opposite sides of the knee brace.

A pair of generally rectangular lateral and medial floating condyle pads 52 and 54 are mounted adjacent the inside faces of the lateral and medial polycentric hinges. Each condyle pad includes inner and outer pieces 56 and 58 of a flexible protective material such as vinyl sandwiching a thin metal piece 59 (see FIG. 5) such as malleable aluminum. Peripheral stitching 60 secures the inner and outer flexible pieces around the internal metal piece which provides a degree of rigidity for the pad. The inner faces of the condyle pads are padded with corresponding layers 62 of a resilient material such as foam rubber or polyurethane foam.

A pair of lateral and medial hinge plates 64 and 66 mount the lateral and medial floating condyle pads to the inner faces of the lateral and medial polycentric hinges. Each hinge plate is a flexible plastic piece such as high density polyethylene or polyproplyene. The plastic piece is generally planar and is divided into first and second flat sections on opposite sides of a hinge line 70, often referred to as a "living hinge". The pivot pins 44 and 48 of the polycentric hinges rigidly attach the first section of the hinges to the inner faces of the inner plates of the polycentric hinges. This prevents the hinge plate from rotating about a horizontal axis at the knee joint. Rivets 68 (shown in FIG. 2) secure the second sections of the plastic hinges to the floating condyle pads. The hinge line 70 on each plastic hinge extends generally vertically adjacent the rear edge of the adjacent polycentric hinge and in front of the point at which the plastic hinge is attached to the condyle pad. The plastic hinges normally maintain the floating condyle pads in a position generally parallel to the vertical planes of the lateral and medial upper and lower arms, as shown best in FIGS. 1, 3 and 4. However, the hinge lines 70 permit the floating condyle pads to bend inwardly through an angle toward each other away from the lateral and medial support arms and into the space between the polycentric hinges. This bending movement of the floating condyle pads illustrated in FIG. 6 is about a generally vertical axis transverse to and spaced to the rear of the horizontal polycentric axis through the polycentric hinges on opposite sides of the brace. This creates an inward tension on the floating condyle pads that can apply a small amount of inward pressure on opposite sides of the knee when the pads are spread apart from their normal position. Inasmuch as the plastic hinges are much smaller in height than the height of the floating condyle pads, which, in turn, are reasonably flexible, the upper and lower portions of the floating condyle pads also are able to bend inwardly toward each other away from the lateral and medial support arms. This bending movement is in the direction of the arrows illustrated in FIG. 4. Thus, the floating condyle pads by their attachment with the plastic hinges have the effect of a universal joint in terms of being bendable about horizontal (front to rear) and vertical axes through the pads.

A flexible elongated upper strap 72 is secured to the inside face of the upper U-shaped support member 12. The inner end of the upper strap is secured to about the midpoint of the upper support member. The upper strap overlies about one-half of the inside face of the upper U-shaped support member and extends to a free end spaced a sufficient distance from the upper support member to allow the upper strap to be wrapped entirely around the patient's upper leg. The upper strap is preferably made from an elastically stretchable material such as gum rubber so the strap can be stretched to fit tightly around the patient's leg.

An attachment is provided for releasably securing the upper strap to the upper U-shaped support member. A flexible attachment piece 74 of fabric is affixed to the inner end of the upper strap. The flexible piece extends over the top and bottom edges to the back side of the U-shaped member. A thistle cloth fastener 76 (preferably of the hook type) on the flexible attachment piece 74 releasably attaches to a cooperating thistle cloth fastener 78 (preferably of the pile type) affixed to the rear face of the upper U-shaped support member. These fasteners are the type commonly sold under the trademark VELCRO. These fasteners provide a means for releasably attaching the inner end of the upper flexible strap to the upper U-shaped support member so the strap can be extended away from either the lateral or the medial side of the upper support member. It is preferable that it extend away from the medial side, as shown.

A fastener 80 of thistle cloth material (preferably of the hook type) is affixed to the inner face of the upper strap adjacent its free end. An elongated fastener 82 of a cooperating type of thistle cloth material (preferably of the pile type) is affixed to the outer face of the upper strap adjacent its attached inner end portion. This section of thistle cloth material extends beyond the edge of the adjacent upper U-shaped support member, and in use, the fastener 80 can be releasably attached to the fastener 82 to hold the upper strap around the patient's upper leg.

A flexible elongated lower strap 84 is secured to the inside face of the lower U-shaped support member 14. The inner end of the lower strap is secured to about the midpoint of the lower support member. The lower strap overlies about one-half of the inside face of the lower support member and extends to a free end spaced a sufficient distance from the lower support member to allow the lower strap to be wrapped entirely around the patient's lower leg. The lower strap is also preferably made from an elastically stretchable material such as gum rubber.

The lower strap is releasably secured to the lower support member by a flexible attachment piece 86 of fabric having a fastener 88 of thistle cloth material (preferably of the hook type) for releasably attaching to a section of thistle cloth material 90 (preferably of the pile type) attached to the back side of the lower U-shaped member. This provides a means for releasably attaching the inner end of the lower flexible strap to the lower U-shaped support member so that the strap can extend away from either the lateral or the medial side of the lower support member. It is preferred that it extend away from the lateral side of the lower support member, as shown.

The releasable attachment of the upper and lower flexible straps to the upper and lower U-shaped support members allows the two straps to extend away from opposite sides of their corresponding U-shaped support members for providing a de-rotation strapping system to be described in more detail below.

A fastener 92 of thistle cloth material (preferably of the hook type) is attached to the inner face of the lower strap 84, and an elongated fastener 94 of a cooperating thistle cloth material (preferably the pile type) is secured to the outer face of the lower strap. This permits the lower strap to be wrapped entirely around the patient's lower leg with the fastener 92 at the outer end of the strap being releasably attached to the fastener 94 on the rear face of the strap for holding the lower strap tightly in place wrapped around the patient's lower leg.

A pair of upper and lower elastic bands 96 and 98 are secured to the floating condyle pads for holding the condyle pads in contact with the lateral and medial sides of the patient's knee joint. Ends of the elastic bands are affixed to the medial condyle pad by rivets 100 and 102 that also secure upper and lower hooks 104 and 106 to the outer face of the medial condyle pad. The end portions of the upper and lower elastic bands are sandwiched inside the vinyl pieces that comprise the medial condyle pad, and the rivets extend through these portions of the pad and the elastic bands for securing the ends of the elastic bands to the condyle pad. The upper and lower elastic bands extend parallel to one another behind the central portion of the brace and are then threaded through loops 108 formed on the outer face of the lateral condyle pad. The upper and lower elastic bands then extend to free ends having slip-type keepers 110 adjacent the free ends of the straps. The keepers are adapted to fasten to the upper and lower hooks when attaching the elastic bands around upper and lower portions of the patient's knee joint.

In use, the knee brace is placed around the knee joint of a patient by first placing the upper and lower legs of the patient within the upper and lower U-shaped support members so that the back portions of the patient's legs are in contact with the inside faces of the upper and lower support members (and the gum rubber straps overlying the inside faces of the upper and lower support members). The brace is positioned so that the polycentric hinges are closely aligned with the horizontal, side-to-side pivot axis through the patient's knee joint. The upper and lower straps are then stretched longitudinally and tightly wrapped around the patient's upper and lower legs for securing the upper and lower U-shaped support members to the patient's upper and lower legs above and below the knee joint. The gum rubber straps overlie the inside faces of the upper and lower support members so the straps can be tightly wrapped in direct contact with the patient's upper and lower legs, which, in part, provides effective de-rotation for the upper and lower legs. The floating condyle pads are securely placed in contact with the lateral and medial sides of the patient's knee joint, and the upper and lower elastic bands carried by the condyle pads are wrapped around the patient's leg above and below the knee joint and fastened for securely holding the condyle pads in contact with opposite sides of the knee joint. The flexible upper strap is stretchable and held in direct contact with the patient's upper leg for a substantial distance around the circumference of the patient's upper leg. Similarly, the lower flexible strap is stretchable and held in direct contact with the patient's lower leg for a substantial distance around the circumference of the patient's lower leg. The upper and lower flexible straps extend in opposite directions around the patient's upper and lower leg, and it has been discovered that by wrapping the upper and lower straps in opposite directions around the patient's upper and lower leg, and by maintaining tight contact with the patient's leg, a successful anti-derotation strapping arrangement is provided, which resists rotation or twisting of the upper leg and lower leg. That is, the upper and lower flexible straps cooperate with the upper and lower U-shaped support members to immobilize the lower leg from twisting relative to the upper leg about a vertical axis.

More specifically, the upper and lower straps can be arranged to extend away from either side of the upper or lower U-shaped support members, depending upon the type of de-rotation that is desired. In many cases, for example, injuries occur to the anterior crutiate ligament and following repair of the ligament it is desirable to prevent outward rotation of the patient's lower leg relative to the upper leg. To prevent this type of rotation, the lower strap is secured to the lower U-shaped member so the lower strap overlies the inside portion and extends away from the inside end of the lower U-shaped member, while the upper strap is secured to the upper U-shaped member so the strap overlies the outer portion and extends away from the outer end of the upper U-shaped member. To prevent inward rotation, on the other hand, the lower strap can be attached to the lower U-shaped member so that the lower strap overlies the outer portion and extends away from the outer end of the lower U-shaped member, and vice versa for the upper strap. When the upper and lower straps are then tightly wrapped in the opposite directions, the desired de-rotation is provided.

The knee brace also limits the movement of the leg to free swinging movement about a horizontal axis (from side-to-side) through the knee joint. The rigidity of the lateral and medial support arms prevents sideways movement of the knee joint. The stops at opposite ends of the polycentric hinge limit extreme contraction and flexion of the leg about the knee joint. Extreme flexion, particularly, can cause stress in the knee.

The lateral and medial floating condyle pads are bendable to match the contour of the sides of the knee joint. The hinge attachments of the condyle pads allow the condyle pads to maintain total contact with the sides of the knee joint through the full range of motion of the knee. The elastic bands hold the floating condyle pads in close contact with the knee joints.

The arrangement of the upper and lower U-shaped support members provides comfort for the patient, since they are secured to the back side of the patient's upper and lower leg, rather than in front of the leg, which otherwise can cause discomfort by causing pressure over the crest of the tibia.

The knee brace adapts to knee joints of various sizes and shapes and can be prefabricated in a few standard sizes, rather than requiring custom fitting.

FIG. 7 shows an alternative form of the invention in which lateral and medial floating condyle pads 112 and 113 are shaped and mounted in an arrangement different from the condyle pads shown in the knee brace of FIGS. 1–6. The floating condyle pads 112 and 113 have opposite inwardly curved or recessed front edges 114 and 116 for conforming to the shape of the patient's kneecap. A patient can suffer from "patella tracking" in which the kneecap can slide from side-to-side. This condition is particularly prevalent after a patient has had an operation involving the knee ligaments. In addition, with certain athletic injuries, there can be a need to hold the kneecap in place restrained against side-to-side movement. The curved front edges 114 and 116 of the floating condyle pads are firmly supported adjacent opposite sides of the kneecap when the knee brace is worn, for preventing side-to-side motion of the kneecap.

FIG. 7 also shows an alternative construction of the hinge plates for mounting the floating condyle pads. In the embodiment of FIG. 7, the inside faces 118 and 120 of the lateral and medial hinge plates provide the entire outer faces of the floating condyle pads. The lateral and medial hinge plates are made from a semi-rigid plastic material such as high density polyethylene or polypropylene. The inside faces of the hinge plates are bonded to the outer faces of the vinyl layers 122 which, in turn, are attached to the resilient foam pads 124 forming the insides of the condyle pads. The lateral and medial hinge plates are folded back on themselves so they are hinged to pivot about vertical hinge lines 126, 128 formed as "living hinges" along the rear edges of the hinge plates.

The outer faces of the lateral and medial hinge plates are formed as small tabs 130, 132 that overlie the inner plates 134, 136 of the lateral and medial polycentric hinges. The pivot pins of the polycentric hinges rigidly affix the lateral and medial tabs to the inside plates of the polycentric hinges. This hinging arrangement applies tension to the floating condyle pads that normally causes the pads to project at an angle into the space between the polycentric hinges, to the normal position shown in FIG. 7, where the recessed front edges of the pads are closely spaced from one another.

The condyle pads can be spread apart against the normal spring-like bias of the hinge plates when applying the knee brace to the patient. When the patient wears the knee brace, the inward tension provided by the hinge plates causes the condyle pads to apply inward pressure to opposite sides of the patient's knee, since the condyle pads will normally be spread apart against the normal inward bias of the hinges when the brace is worn. This not only causes the floating condyle pads to provide support against opposite sides of the patient's knee during full rotational movement of the knee, but it also provides a spring-biased support for the opposite front edges 114, 116 of the codyle pads against the sides of the patient's patella to resist patella tracking.

I claim:

1. A knee brace comprising:
   upper and lower limb support members;
   means for securing the upper and lower limb support members to the upper and lower legs above and below the knee joint;
   a pair of upper support arms extending down from the upper limb support member for extending along opposite sides of the upper leg to remote ends adjacent lateral and medial sides of the knee joint;
   a pair of lower support arms extending upwardly from the lower limb support member for extending along opposite sides of the lower leg toward remote ends adjacent lateral and medial sides of the knee joint;
   lateral and medial pivot means interconnecting the remote ends of the upper support arms with the remote ends of corresponding lower support arms for providing relative pivotal movement of the upper and lower support arms adjacent the lateral and medial sides of the knee joint, said pivotal movement being about a generally horizontal axis, the lateral and medial pivot means each having a fixed portion adjacent lateral and medial sides of the knee joint so the corresponding upper and lower support arms pivot relative to the fixed portions of the pivot means;
   lateral and medial condyle pads for contacting lateral and medial sides of the knee joint; and
   lateral and medial hinge means affixed to the lateral and medial condyle pads and hinged to the fixed portions of the lateral and medial pivot means for mounting the condyle pads between the lateral and medial pivot means, so the condyle pads can be placed in direct contact with the lateral and medial sides of the knee joint, the lateral and medial hinge means allowing the lateral and medial condyle pads to each pivot through an angle relative to the fixed portions of the pivot means and about a generally vertical axis toward and away from each other, such pivotal movement of the condyle pads being within the space between the lateral and medial pivot means.

2. Apparatus according to claim 1 in which each pivot means comprises a polycentric hinge.

3. Apparatus according to claim 1 in which the fixed portion of each pivot means includes a fixed base and at least one pivot pin for pivoting at least one of the upper or lower support arms to the fixed base; and in which each hinge means is hinged to a corresponding fixed base.

4. Apparatus according to claim 3 in which each hinge means comprises a hinge plate having a hinge line between a first portion and a second portion of the plate; and in which the first portion of the hinge plate is rigidly affixed to the fixed plate of the pivot means, and in which the second portion is rigidly affixed to a corresponding condyle pad.

5. Apparatus according to claim 4 in which the hinge means is a plastic plate with the first and second portions being foldable about a linear hinge line.

6. Apparatus according to claim 1 in which the securing means includes an upper flexible strap secured to the upper limb support member for extending away from one side of the upper limb support member, and a lower flexible strap secured to the lower limb support member for extending away from a side of the lower limb support member opposite from the side that the upper flexible strap extends away from the upper support member.

7. Apparatus according to claim 6 including means for releasably securing the upper strap and the lower strap to the upper and lower limb support members.

8. Apparatus according to claim 6 in which at least a portion of the upper flexible strap and the lower flexible strap overlies an inside portion of the upper and lower limb support members.

9. Apparatus according to claim 1 in which the condyle pads have recessed front edges for conforming to the shape of opposite sides of the patient's kneecap, and in which the hinge means support the recessed front edges of the condyle pads against opposite sides of the kneecap.

10. Apparatus according to claim 1 in which the hinge means include means for spring biasing the condyle pads toward the space between the pivot means.

11. A knee brace comprising:
   upper and lower limb support members;
   a pair of upper support arms extending down from the upper limb support member for extending along opposite sides of the upper leg to remote ends adjacent lateral and medial sides of the knee joint;
   a pair of lower support arms extending upwardly from the lower limb support member for extending along opposite sides of the lower leg to remote ends adjacent lateral and medial sides of the knee joint;
   lateral and medial pivot means interconnecting the remote ends of the upper support arms with corresponding remote ends of the lower support arms for providing relative pivotal movement of the upper and lower support arms so they pivot about a generally horizontal axis adjacent the lateral and medial sides of the knee joint;
   an upper flexible strap secured to the upper limb support member for extending away from one side of the upper limb support member for securing the upper limb support member to the upper leg above the knee joint; and a lower flexible strap secured to the lower limb support member for extending away from an opposite side of the lower limb support member from the side away from which the upper flexible strap extends away from the upper limb support member for securing the lower limb support member to the lower leg below the knee and for wrapping the two straps in opposite directions around the upper and lower leg to provide a de-rotation means for securing the brace to the upper and lower leg.

12. Apparatus according to claim 11 in which the upper and lower flexible straps are elastically stretchable longitudinally.

13. Apparatus according to claim 11 including means for releasably securing the upper and lower flexible straps to the upper and lower support members.

14. Apparatus according to claim 1 in which each hinge means comprises a hinge plate having a hinge axis between a first portion and a second portion of the plate; in which the first portion of the hinge plate is rigidly affixed to the fixed plate of the pivot means; and in which the second portion is rigidly affixed to a corresponding condyle pad.

15. Apparatus according to claim 14 in which the second portion of the hinge plate is normally spring biased inwardly toward the space between the pivot means so the condyle pad applies tension to the side of the knee joint when the condyle pad is urged outwardly under the bias of the hinge plate.

16. Apparatus according to claim 15 in which the hinge plate is a plastic plate having a living hinge along the hinge axis, and the plate is folded back on itself so the second portion of the plate normally projects at an angle into the space between the pivot means.

* * * * *